United States Patent [19]
Hodgson et al.

[11] Patent Number: 5,856,539
[45] Date of Patent: Jan. 5, 1999

[54] FATTY ACID ISOMERISATION

[75] Inventors: William R. Hodgson, Bebington Wirral, Great Britain; Wicher Tijmen Koetsier, Emmerich, Germany; Cornelis Martinus Lok, Bebington Wirral; Glyn Roberts, Bebington, both of Great Britain

[73] Assignee: Unichema Chemie B.V., Gouda, Netherlands

[21] Appl. No.: 751,570

[22] Filed: Nov. 18, 1996

[30] Foreign Application Priority Data

Nov. 16, 1995 [EP] European Pat. Off. ............. 95308224

[51] Int. Cl.$^6$ .................................................. C07C 51/353
[52] U.S. Cl. ................................................ 554/125
[58] Field of Search ................................. 554/125

[56] References Cited

FOREIGN PATENT DOCUMENTS 0 683 150 A1  11/1995   European Pat. Off. ...... C07C 51/353
WO 91/06616   5/1991    WIPO .......................... C10G 35/095

*Primary Examiner*—Paul J. Killos
*Attorney, Agent, or Firm*—Pillsbury Madison & Sutro LLP

[57] ABSTRACT

It was found that the conversion (by isomerisation or branching) of unsaturated fatty acids into branched fatty acids can be catalysed by materials having a microporous structure. Such a process gives high conversion rates and a high selectivity towards branched fatty acids, whilst a low amount of undesired by-products is obtained. Zeolites are preferred materials for catalysing said reaction.

22 Claims, No Drawings

FATTY ACID ISOMERISATION

The present invention relates to a chemical process, and in particular to a process for the isomerisation (branching) of fatty acids in which a catalyst is employed. In said process, the fatty acid feed to be processed comprises unsaturated fatty acids.

Fatty acids are versatile building blocks in various parts of the chemical industry, ranging from lubricants, polymers, solvents to cosmetics and much more. Fatty acids are generally obtained by hydrolysis of triglycerides of vegetable or animal origin. Naturally occurring triglycerides are esters of glycerol and generally straight chain, even numbered carboxylic acids, in size ranging from 10–24 carbon atoms. Most common are fatty acids having 12, 14, 16 or 18 carbon atoms. The fatty acids can either be saturated or contain one or more unsaturated bonds.

Long, straight chain saturated fatty acids (C10:0 and higher) are solid at room temperature, which makes them difficult to process in a number of applications. The unsaturated long chain fatty acids like e.g. oleic acid are liquid at room temperature, so are easy to process, but are unstable because of the existence of double bond(s). Branched fatty acids mimic the properties of the straight chain unsaturated fatty acids in many respects. However, they do not have the disadvantage of being unstable. For example branched C18:0 fatty acid (commercially known as isostearic acid) is liquid at room temperature, but is not as unstable as C18:1, since unsaturated bonds are absent in branched C18:0. Therefore, branched fatty acids are for many applications more desirable than straight chain fatty acids. (The term "branched fatty acids" is herein to be understood to comprise fatty acids which contain one or more alkyl side groups, which can be attached to the carbon chain at any position. Said alkyl groups are generally short.)

Currently, branched fatty acids are obtained by isomerisation (branching) of the straight chain, unsaturated fatty acids having a corresponding chain length. For example, branched C18:0 is prepared from straight C18:1 (or also C18:2).

Among the routes known for said isomerisation or branching is a reaction in which clay is used as a catalyst. This clay catalysed isomerisation suffers from two main disadvantages, the most important one being the fact that besides the formation of the desired branched fatty acids, a considerable amount of undesired side products (containing oligomers, saturated straight chain fatty acids and intermediate dimers) is formed (30–40% by weight). The formation of intermediate dimer is particularly disadvantageous, since these represent very low value products. A second disadvantage is that the clay catalyst cannot be reused.

Hence, there is a need for a new process overcoming these disadvantages, i.e. a process for the preparation of branched fatty acids from straight chain unsaturated fatty acid feedstocks with an increased selectivity towards branched monomeric isomers versus oligomeric species. Such a process should preferably still give high conversion of reactants and employ a reusable catalyst.

It has now been found that it is possible to convert (by isomerisation) a feed of fatty acids comprising fatty acids containing at least one unsaturated carbon-carbon bond (such as e.g. oleic acid) into a mixture which is rich in branched fatty acids and low in oligomers. Preferably, the isomerisation involves branching. In said process a fatty acid feed comprising unsaturated fatty acids is contacted with a catalyst, characterized in that the catalyst comprises a material having a microporous structure. It is herein to be understood that the reaction product will generally comprise both saturated as well as unsaturated branched fatty acids, and both are thus included in the invention. Optionally, the unsaturated branched fatty acids may be hydrogenated in any conventional way. The reaction which is the subject of this invention can be seen as an isomerisation reaction (involving both skeletal and positional isomerisation). The branching reaction is herein included.

Such a material having a microporous structure includes zeolites and microporous materials having a zeolite structure such as aluminium phosphates (AlPO's), metal aluminophosphates (MeAPO's) and silico alumino phosphates (SAPO's). Zeolites are for the purpose of this invention preferred.

Preferably, the zeolite in said process posesses a unidimensional pore topology. A preferred zeolite of this type is mordenite. Zeolites are crystalline aluminosilicates which can be represented by the general formula $M_{p/n}[AlO_2]_p (SiO_2)_{192-p}].qH_2O$, where M is a metal cation of groups IA (including Hydrogen) or IIA and n is the valency of this metal. Zeolites consist of a microporous network of $SiO_4$ and $AlO_4$ tetrahedra linked together via shared oxygen atoms. Aluminum has a 3+ valency resulting in an excess negative charge on the $AlO_4$ tetrahedra, which can be compensated by $H^+$ or other cations ($Na^+$, $NH_{4+}$, $Ca^{2+}$). When M is hydrogen the materials are Bronsted acidic, when M is for example Cs the materials are basic. Upon heating, Bronsted acidic hydroxyls condense creating coordinately unsaturated Al, which acts as a Lewis acid site. The acid strength, acid site density and Bronsted versus Lewis acidity are determined by the level of framework aluminium. The ratio of silica/alumina can be varied for a given class of zeolites either by controlled calcination, with or without the presence of steam, optionally followed by extraction of the resulting extraframework aluminium or by chemical treatment employing for example ammonium hexafluorosilicate. It has been found that, when mordenite is used as a catalyst, for achieving the desired branched fatty acid selectivity whilst maintaining a good conversion of unsaturated fatty acids, the ratio of $SiO_2/Al_2O_3$ in the mordenite is preferably at least 14, more preferably at least 20, and most preferably at least 35 (said ratio was measured using X-ray fluorescence).

Another preferred class of zeolites for performing the reaction according to the invention are the zeolites belonging to the classes of zeolites L and zeolite omega. Zeolites L (including their preparation) have been described in WO 91/06367. Zeolites omega have been described in GB 1,178,186.

It has been found that for good selectivity whilst maintaining a good conversion it is preferred that at least part of the isomerisation is performed at a temperature of between 200° C. and 320° C., and more preferably a temperature of between 230° C. and 285° C. Since the conversion is also a function of the reaction time, it is preferred that the fatty acid feed is contacted with the catalyst for a period of at least 30 minutes. More preferred are reaction times of 1–16 hours. In general, the amount of catalyst employed in the process according to the invention is between 0.5 and 20% by weight, based on the total reaction mixture. More preferably is an amount of catalyst used between 2.5 and 10% by weight. Most preferred are amounts between 3 and 7% by weight.

In EP-A 683 150 it is mentioned that reactions similar to the reaction according to this invention should be carried out in the presence of water or a lower alcohol. However, applicants have found that this is not always needed. Hence, it may be preferred to perform the reaction as set out above, without adding water or a lower alcohol, or, alternatively, in the absence of water or a lower alcohol.

It has been found that by using the catalyst system according to this invention it is possible to reuse the catalyst after a first reaction cycle. In some cases it may be desired to add fresh catalyst (while bleeding off part of the used catalyst), and in other cases regeneration of the catalyst may be desired. Regeneration can be effected by heating the used catalyst in an inert atmosphere (e.g. nitrogen) to 450°–650° C. (preferably to about 550° C.), although controlled oxidative regeneration may be employed too. Regeneration may be effected by washing with a solvent.

Since the process according to the invention is designed for isomerisation or conversion of unsaturated fatty acids into branched fatty acids, it is beneficial if the fatty acid feed comprises of at least 50% by weight of unsaturated fatty acids, more preferably at least 80% by weight of unsaturated fatty acids. A preferred unsaturated fatty acid to be present in the fatty acid feed is oleic acid. It is preferred that the fatty acid feed comprises at least 40% by weight of oleic acid, more preferably at least 70% by weight oleic acid. The feedstock may comprise polyunsaturated fatty acids.

Applicants have furthermore found that for carrying out the process according to the invention it is preferred that in the case in which the catalyst employed is a zeolite, the morphology and/or crystallite size of the zeolite material in addition to pore topology are of importance.

As indicated before, zeolites having uni-dimensional pores are preferred. Such zeolites are also described as having a linear pore structure. Even more surprising than the influence of the pore geometry is the fact that the shape or morphology of the zeolite crystallites is of importance. The crystallite morphology can accurately be quantified by measuring the crystallite diameter and the crystallite depth. Most suitable for comparison purposes is measurement of the maximum crystallite diameter (L) and the maximum crystallite depth (D). These can be measured using (a combination of) scanning electron microscopy (SEM) and/or transmission electron microscopy (TEM). How this can be done is set out in detail in WO 91/06367. From the measured L and D values, both in micrometer, one can calculate the aspect ratio L/D.

It has surprisingly been found that for good results (in terms of optimal reactivity and low amounts of trimer and oligomers formed) it may be preferred that the L/D ratio (crystallite aspect ratio) is larger than 8. More preferably, this ratio should be larger than 12. It is even more preferred that this ratio is at least 10, and it is most preferred that this ratio is at least 20.

The invention will be illustrated by the following examples, which should not be interpreted as limiting the scope of the invention thereto.

EXAMPLE 1:

Evaluation of commercial mordenites.

A feedstock essentially consisting of (percentages by weight):
97.4% C18:1 (oleic acid)
4.0% C16:0
1.3% C14:0
trace C18:0
was subjected to a range of isomerisation experiments.

Evaluation Procedure

In a one-litre Parr autoclave were mixed: 300 grams of feedstock and the desired amount of the chosen catalyst. The reactor was evacuated with nitrogen, and subsequently heated to the desired temperature. The evacuating step involves pressurising the reactor to 5 bar and stirring at 600 rpm followed by releasing the pressure. This procedure was repeated twice with the reaction vessel finally pressurized to 1 atmosphere with nitrogen. The reactor is then maintained at the reaction temperature for the chosen reaction time, whereafter the reactor is cooled to room temperature.

The amount of catalyst ranged from 1.3 to 5% by weight. The temperature ranged from 250° C. to 275° C. The reaction time ranged from 1 to 6 hours.

The clay used was a naturally occurring montmorillonite clay, composition $SiO_2$(64 w/w %), $Al_2O_3$(17 w/w %), $Fe_2O_3$(5 w/w %), CaO(1.5 w/w %), MgO(4 w/w %). The mordenite used was of formula: $Na_2O.Al_2O_3.10SiO_2.6H_2O$, type CBV10AH as marketed by PQ (USA). Other types tested were CBV20A and CBV 30A (see table 2).

Analysis of the product mix was performed by first converting the monomer, dimer and trimer mixture into its methyl derivatives by refluxing in a $BF_3$/methanol mixture (12 w/w % $BF_3$—ex-Aldrich). The procedure for performing the derivatisation involved weighing approximately 0.15 g of the total product into a 50 ml round bottomed flask. To this was added 2 ml of the $BF_3$/methanol complex and the mixture was heated to reflux, in a standard water condenser/reaction flask arrangement, for 2 minutes. Two mls of heptane was added to the flask via the condenser and refluxed for a further two minutes. Following this, the mixture was allowed to cool to room temperature, at which point sufficient saturated NaCl solution was added to bring the resultant methylated esters into the neck of the flask. The organic/methylated layer was then transferred by pipette into a sample tube containing anhydrous sodium sulphate and diluted to five times it's volume with heptane, and the resultant mixture filtered.

The methyl esters were evaluated with a gas chromatograph equipped with a flame ionisation detector and fitted with a J&W Scientific 15 w 0.32 widebore DB5HT capillary column. Analysis of the concentration of branched fatty acids present in the monomer fraction was performed by first distilling approximately 20 mls of total product in a "Kugelrohr" apparatus. The distillation was carried out under a strong vacuum at 250° C. Once the desired temperature was reached the distillation was allowed to continue for about 10 minutes to ensure all the monomer has been distilled off. The monomer was collected and diluted in heptane (1:10) ready for analysis. Analysis was performed with a gas chromatograph fitted with a J&W Scientific 30m 0.25 narrowbore FFAP column with a film thickness of 0.25 microns.

Results

The values of isostearic acid (ISA) obtained were calculated using the following expression:

total yield ISA (%)={[ISA]/[Monomer]}×[Monomer]$_{TP}$ where the ratio [ISA/Monomer] refers to the concentration of isostearic acid (w/w %) present in the distilled monomer fraction and [Monomer]$_{TP}$ is the concentration of monomer (w/w %) present in the total product following esterification.

Similarly the levels of oleic and stearic acid are calculated using the following expressions:

Oleic acid(w/w %)={[Oleic acid]/[Monomer]}×[Monomer]$_{TP}$

Stearic acid (w/w %)={[Stearic acid]/[Monomer]}×[Monomer]$_{TP}$

The results are set out in tables 1, 2 and 3. In the tables, the following codes are used:

ISA: isostearic acid (branched C18, including saturated and unsaturated isostearic acid).
StA: stearic acid (C18:0, straight chain)
OA: oleic acid (C18:1, straight chain)
ID: intermediate dimer (mixture of partly dimerized, partly branched, but containing more than 18 carbon atoms)
DIM: Dimers (C36 dibasic acids)
TRIM: Trimers (C54 tribasic acids).

In table 1, the mixtures obtained using clay and mordenite as a catalyst system can be compared. The catalyst loading (amount of of clay/zeolite) was 5% by weight. As can be seen, the use of mordenite leads to the formation of low amount(s) of oligomers. Regarding the use of mordenite, the influence of temperature and reaction time can also be seen in table 1. In table 2 (also catalyst loading 5% by weight), the influence of the silica:alumina ratio can be seen. In table 3, the influence of using different loadings of mordenite catalyst can be observed.

EXAMPLE 2:

Effect of Re-use of Catalyst.

In a set up identical to example 1 above, various re-use procedures have been tested. Re-use has been performed on mordenite CBV30A.

Re-use has been tested without reactivating the catalyst employed between two cycles. After a first cycle, the catalyst was obtained from the reaction medium by centrifuging the catalyst from the total product, whereafter the reaction was started again, using fresh oleic acid. Thermal analysis (TGA) on the centrifuged product showed that the centrifuged catalyst contained about 35% solid and about 65% residual total product. Thus, in order to have 15.8% of mordenite catalyst, 45 g of the centrifuged product was added to 300 g of oleic acid.

Re-use has been performed for reaction times of 4 hours (similar to example 1) and also for reaction times of 8 hours. Also, a re-use cycle has been performed in which part of the catalyst was re-used (90%), the remainder being replaced with fresh catalyst. The results are displayed in table 4.

EXAMPLE 3:

Evaluation of Zeolites L and Omega.

In a process identical to the process for testing the mordenite catalysts (example 1) three other uni-dimensional catalysts have been tested: zeolite Omega and zeolite L, the latter in two forms: HL1 and HL2. Zeolite Omega has been prepared according to the process as disclosed in GB 1178186. Both zeolites L have been prepared according to the process of Aeillo and Barrer, J. Chem. Soc., A, 1470 (1970), see also example 4 below. Zeolite HL1 was prepared under stirred conditions, HL2 under static conditions. The zeolites L (HL1 and HL2) and omega were prior to use ion exchanged, in order to yield the proton form of the zeolite. This procedure involved refluxing 20 g of zeolite in 200 ml of 0.5M ammonium chloride solution for 2 hours. The resultant slurry was allowed to cool to room temperature and then filtered and washed with 3 litres of boiling demineralised water. This process was repeated twice and the resultant zeolite dried at 100° C. overnight. Prior to catalytic evaluation, all of the zeolite were calcined at 400° C. for 1 hour in a shallow bed. This latter procedure leads to decomposition of the ammonium ion to yield the proton form of the zeolite and also results in water removal from the zeolite pore channels.

The process used for evaluating the catalyst was identical as in example 1, with the following settings:

amount of zeolite: 7.9 g (2.5% by weight)
reaction temperature: 250° C.
reaction duration: 4 hours.

Analysis of the obtained reaction product was performed in the same manner as in example 1. The results of the analysis are shown in table 5.

EXAMPLE 4:

Effect of Uni-dimensional Zeolite Crystal Morphology.

Zeolite HL1

K form zeolite L was prepared using the recipe described by Aeillo and Barrer, J. Chem. Soc., A, 1470 (1970). The procedure involves adding 51.6 g of potassium hydroxide, 2.75 g aluminium wire, 61.4 g fumed silica (CARBOSIL M5) and 284.5 g of distilled water into a Teflon autoclave liner and mixing thoroughly. The resultant gel was then aged at 100° C. in a sealed autoclave for 9 days, in order to affect crystallisation. Following crystallisation the slurry was centrifuged at 3000 rpm for 30 mins, in order to separate the zeolite form the mother liquor. The resultant zeolite was washed with demineralised water and re-centrifuged at 3000 rpm for a further 30 mins. This yielded a zeolite with the following molar composition.

Zeolite composition—$9K_2O:Al_2O_3:20SiO_2:315H_2O$

Zeolite HL2

K form zeolite L was prepared using the recipe described by Aeillo and Barrer, J. Chem. Soc., A, 1470 (1970). The procedure involves adding 51.6 g of potassium hydroxide, 2.75 g aluminium wire, 61.4 g fumed silica (CARBOSIL M5) and 284.5 g of distilled water into a Teflon autoclave liner and mixing thoroughly. The resultant gel was then aged at 100° C. with continual stirring at 300 rpm, in a sealed autoclave for 8 days, in order to affect crystallisation. Following crystallisation the slurry was centrifuged at 3000 rpm for 30 mins, in order to separate the zeolite form the mother liquor. The resultant zeolite was then washed with demineralised water and re-centrifuged at 3000 rpm for a further 30 mins. This yielded a zeolite with the following molar composition.

Zeolite composition—$9K_2O:Al_2O_3:20SiO_2:315H_2O$

Zeolite HL3

A sample of zeolite L was prepared according to the method described by Verduijn, EP-A 219 354. This method involves dissolving aluminium hydroxide in a boiling aqueous solution of potassium hydroxide pellets (86% pure KOH) to yield solution A. After dissolution water loss was corrected by addition of demineralised water. A separate solution, solution B, was prepared by diluting colloidal silica (Ludox HS40) with water.

The two solutions were mixed for two mins to form a gel, and just before the gel became fully set, the mixture was transferred to a Teflon-lined autoclave, preheated to 150° C. The autoclave was maintained at this temp for 72 h to affect crystallisation. Following crystallisation the slurry was centrifuged at 3000 rpm for 30 mins, in order to separate the zeolite form the mother liquor. The resultant zeolite was then washed with demineralised water and re-centrifuged at 3000 rpm for a further 30 mins. This yielded a zeolite with the following molar composition.

Zeolite composition—$2.6K_2O:Al_2O_3:10SiO_2:160H_2O$

Zeolite HL4

A sample of zeolite L was prepared according to the method described by Verduijn, WO 91/06367. This method involves dissolving 7.91 g of aluminium hydroxide in a boiling aqueous solution of KOH. The latter was prepared by dissolving 34.30 g of KOH pellets in 50.10 g of water. The KOH/Al(OH)$_3$ solution (denoted solution A) was allowed to cool to room temperature prior to further experimentation A separate solution was prepared by adding 150.26 g of colloidal silica (Ludox HS—40) and 50.01 g of water. To this was added a solution prepared by dissolving 0.1 g of Ba(OH)$_2$8H$_2$O crystals in 25 g of water. The resultant solution was stirred for 5 mins and solution A added, together with 64.47 g of water. The mixture was stirred for a further 3 mins and the resultant synthesis mixture transferred to a stainless steel autoclave. The autoclave was placed in an oven and heated to 170° C. and maintained at this temperature for 96 hrs.

The product was separated from the mixture by centrifuging, washed to pH 9.7 and dried overnight at 150° C. This yielded a zeolite L with the following composition.

Zeolite composition—
2.65K$_2$O:0.0032BaO:0.5Al$_2$O$_3$:10SiO$_2$:159H$_2$O

Zeolite HL5 and zeolite HL6

In addition to the synthesised materials, two further L form zeolites were obtained from commercial suppliers (HSZ-500KOA (ex-Tosoh Corporation)—denoted HL5 in this study and Zeocat L (ex-Uetikon)—denoted HL6.

All of the above samples were ion-exchanged in order to yield the proton form of the zeolite. The procedure adopted involved refluxing 20 g of the chosen zeolites in 200 ml of 0.5M ammonium chloride solution for 2 h. The resultant slurry was allowed to cool to room temperature and then filtered and washed with 3 litres of boiling water. The process was repeated twice and the resultant zeolite dried at 400° C. for 1 h in a shallow bed in order to decompose the the ammonium ion and yield the zeolite in the proton form. Following ion—exchange the zeolites are hereafter referred to as HL1-6, where the number refers to the example aboves.

X-ray diffraction confirmed that all these materials were zeolite L structures, while $^{27}$Al NMR studies confirmed that in excess of 90% of the aluminium was present within the framework of the zeolites.

Mordenites

Commercial mordenites were also evaluated, these comprised CBV30A and CBV20A (ex-PQ) and HSZ620HOA, HSZ640HOA, and HSZ690HOA (ex-Tosoh Corporation). All of these are supplied in the proton form and were characterised and evaluated without additional treatments.

X-ray diffraction confirmed that all these materials possessed mordenite structures, while $^{27}$Al NMR studies confirmed that in excess of 85% of the aluminium was present within the framework of the zeolites.

The morphologies and crystallite sizes determined by a combination of scanning electron microscopy (SEM) and transmission electron microscopy (TEM) are summarised in Table 6. L refers to the maximum crystallite diameter, D to the maximum crystallite depth and the parameter L/D (diameter/depth) is the aspect ratio for the crystals.

Scanning electron microscopy (SEM) was perfomed on all samples following carbon coating, using a Cambridge S360 electron microscope. Transmission electron microscopy (TEM) was performed on a JEOL200CX transmission electron microscope at 80 kV following dispersal of the sample in isopropanol.

The aspect ratios for the mordenites were found to vary from 1.5–10, while those of the L zeolites varied from 0.25–20.

Catalyst evaluaton in fatty acid branching/ oligomerisation

All of the catalysts were evaluated exactly as described in the evaluation procedure as above in example 1. Catalyst concentrations (loading) were 2.5 w/w % for all catalysts. A summary of the obtained selectivities is given in Table 7. In table 7, the same headings are the same as those used in Table 1.

TABLE 1

Yields comparing clay with unidimensional zeolite (CBV10AH) (Mordenite catalyst loading 5%)

| catalyst | time (h) | temp (°C.) | % ISA | % StA | % OA | % ID | % DIM | % TRIM |
|---|---|---|---|---|---|---|---|---|
| clay | 4 | 250 | 46 | 12 | 7 | 6 | 29 | 4 |
| mordenite | 4 | 250 | 53 | 12 | 20 | 7 | 11 | 0.6 |
| mordenite | 4 | 265 | 68 | 14 | 7 | 2 | 8 | <0.1 |
| mordenite | 4 | 275 | 60 | 26 | 7 | 0.5 | 7 | <0.1 |
| mordenite | 6 | 250 | 66 | 15 | 10 | 1 | 8 | 0.1 |

TABLE 2

Yields using mordenite (catalyst loading 5% by weight), different ratios of SiO$_2$/Al$_2$O$_3$

| SiO$_2$/Al$_2$O$_3$ ratio of mordenite | time (h) | temp (°C.) | % ISA | % StA | % OA | % ID | % DIM | % TRIM |
|---|---|---|---|---|---|---|---|---|
| 14 (CBV10AH) | 4 | 250 | 16 | 6 | 61 | 8 | 9 | 0.1 |
| 20 (CBV20A) | 4 | 250 | 37 | 7 | 36 | 11 | 8 | 0.3 |

TABLE 2-continued

Yields using mordenite (catalyst loading 5% by weight), different ratios of $SiO_2/Al_2O_3$

| $SiO_2/Al_2O_3$ ratio of mordenite | time (h) | temp (°C.) | % ISA | % StA | % OA | % ID | % DIM | % TRIM |
|---|---|---|---|---|---|---|---|---|
| 35 (CBV30A) | 4 | 250 | 53 | 12 | 20 | 7 | 11 | 0.6 |

TABLE 3

The effect of catalyst loading (Mordenite CBV30A, 4h, 250° C.)

| Catalyst loading (w/w %) | % ISA | % StA | % OA | % ID | % DIM | % TRIM |
|---|---|---|---|---|---|---|
| 5.0 | 53 | 12 | 20 | 7 | 11 | 0.6 |
| 2.5 | 48 | 8 | 36 | 0 | 9.0 | 0.2 |
| 1.3 | 25 | 7 | 58 | 0 | 9.5 | 0.2 |

TABLE 4

The effect of catalyst re-use, without reactivation (Mordenite CBV30A)

| Process | time (h) | % ISA | % StA | % OA | % ID | % DIM | % TRIM |
|---|---|---|---|---|---|---|---|
| no re-use | 4 | 53 | 12 | 20 | 7 | 11 | 0.6 |
| straight re-use | 4 | 40 | 9 | 34 | 8 | 9 | 0.2 |
| straight re-use | 8 | 51 | 11 | 18 | 10 | 10 | 0.3 |
| 90% re-used, 10% fresh | 4 | 48 | 10 | 24 | 8 | 10 | 0.4 |

TABLE 5

Yields comparing various unidimensional zeolites (loading 2.5%).

| Catalyst type | % ISA | % StA | % OA | % ID | % DIM | % TRIM |
|---|---|---|---|---|---|---|
| Omega | 24 | 9 | 42 | 19 | 6 | trace |
| HL1 | 51 | 14 | 16 | 18 | 3 | — |
| HL2 | 51 | 13 | 10 | 18 | 9 | — |

TABLE 6

Summary of morphology and crystallite dimensions as determined by a combination of SEM and TEM.

| Catalyst | Morphology | L/μm | D/μm | L/D |
|---|---|---|---|---|
| M30A | Flat hexagonal discs | 1.0 | 0.1 | 10 |
| M20A | Flat hexagonal discs | 1.0 | 0.1 | 10 |
| 620HOA | Hexagonal discs | 5.0 | 2.5 | 2 |
| 640HOA | Hexagonal discs | 5.0 | 2.0 | 2.5 |
| 690HOA | Mostly Cubic crystals with some needlelike crystals | 2.0 | 0.25 | 8 |
| HL1 | Flat circular plates | 1.0 | 0.05 | 20 |
| HL2 | Irregular particles | 0.5 | 0.05 | 10 |
| HL3 | Cylinders | 0.2 | 0.8 | 0.25 |
| HL4 | Flat plates and needles | 2.0 | 0.5 | 4 |
| HL5 | Flat circular discs | 0.5 | 0.1 | 5 |
| HL6 | Cylinders | 2.0 | 2.0 | 1 |

TABLE 7

Summary of % isostearic acid, stearic acid, oleic acid, intermediate dimer, dimer and trimer obtained using various mordenite and L zeolites as catalysts.

| Catalyst | % ISA | % SA | % OA | % ID | % DIM | % TRIM |
|---|---|---|---|---|---|---|
| M30A | 48 | 13 | 30 | — | 9 | trace |
| M20A | 30 | 6 | 57 | — | 7 | trace |
| 620HOA | 2 | — | 94 | — | 4 | — |
| 640HOA | 9 | 3 | 83 | — | 5 | — |
| 690HOA | 1 | — | 97 | — | 2 | — |
| HL1 | 51 | 14 | 16 | 18 | 3 | — |
| HL2 | 51 | 13 | 10 | 18 | 9 | — |
| HL3 | 4 | 2 | 89 | — | 6 | — |
| HL4 | 2 | 1 | 94 | — | 3 | — |
| HL5 | 3 | 4 | 84 | — | 9 | 0.4 |
| HL6 | 3 | 0 | 91 | — | 5 | 0.4 |

We claim:

1. In a process for the isomerisation of fatty acids, in which a fatty acid feed comprising unsaturated fatty acids is contacted with a catalyst, the improvement wherein the catalyst comprises a material having a microporous structure.

2. Process according to claim 1, wherein the isomerisation of fatty acids comprises branching of the fatty acids.

3. Process according to claim 1, wherein the material having a microporous structure comprises a zeolite.

4. Process according to claim 1, wherein the zeolite comprises a zeolite having a uni-dimensional pore system.

5. Process according to claim 3 or 4, wherein the zeolite comprises mordenite, zeolite L and/or zeolite omega.

6. Process according to claim 5, wherein the ratio of $SiO_2/Al_2O_3$ in the mordenite is at least 14, and more preferably at least 20, and most preferably at least 35.

7. Process according to claim 1, wherein the fatty acid feed comprises of at least 50% by weight of unsaturated fatty acids.

8. Process according to claim 7, wherein the fatty acid feed comprises of at least 80% by weight of unsaturated fatty acids.

9. Process according to claim 1, wherein the fatty acid feed comprises at least 40% by weight of oleic acid.

10. Process according to claim 9, wherein the fatty acid feed comprises of at least 70% by weight oleic acid.

11. Process according to claim 1, wherein at least part of the isomerisation is performed at a temperature of between 200° C. and 320° C.

12. Process according to claim 11, wherein at least part of the isomerisation is carried out at a temperature of between 230° C. and 285° C.

13. Process according to claim 1, wherein the fatty acid feed is contacted with the catalyst for a period of at least 30 minutes.

14. Process according to claim 13, wherein the fatty acid feed is contacted with the catalyst for a period of 1–16 hours.

15. Process according to claim 1, wherein the catalyst is reused without reactivation.

16. Process according to claim 1, wherein the catalyst is reused following reactivation.

17. Process according to claim 1, wherein the amount of catalyst used is between 0.5 and 20% by weight.

18. Process according to claim 17, wherein the amount of catalyst used is between 3 and 7% by weight.

19. Process according to claim 1, wherein the ratio L/D, wherein L refers to the the maximum crystallite diameter and D to the maximum crystallite depth of the zeolite cystallites, is larger than 8.

20. Process according to claim 19, wherein the ratio L/D is at least 10.

21. Process according to claim 20, wherein the ratio L/D is at least 20.

22. In a process for the isomerisation of fatty acids, in which a fatty acid feed comprising unsaturated fatty acids is contacted with a catalyst, the improvement wherein the catalyst comprises a zeolite material having a microporous structure whereby said feed is converted into a mixture which is rich in branched fatty acids and low in oligomers.

* * * * *